US009872934B2

(12) United States Patent
Hedrich et al.

(10) Patent No.: US 9,872,934 B2
(45) Date of Patent: Jan. 23, 2018

(54) HEMOSTATIC SPONGE

(71) Applicants: BAXTER INTERNATIONAL INC., Deerfield, IL (US); BAXTER HEALTHCARE SA, Glattpark (Opfikon) (CH)

(72) Inventors: Hans Christian Hedrich, Vienna (AT); Joris Hoefinghoff, Vienna (AT); Woonza M. Rhee, Palo Alto, CA (US); Atsushi Edward Osawa, San Francisco, CA (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 8 days.

(21) Appl. No.: 15/366,175

(22) Filed: Dec. 1, 2016

(65) Prior Publication Data

US 2017/0080119 A1  Mar. 23, 2017

Related U.S. Application Data

(63) Continuation of application No. 14/320,064, filed on Jun. 30, 2014, now Pat. No. 9,517,287, which is a
(Continued)

(51) Int. Cl.
*A61M 1/00* (2006.01)
*A61M 27/00* (2006.01)
(Continued)

(52) U.S. Cl.
CPC .......... *A61L 15/425* (2013.01); *A61F 13/025* (2013.01); *A61F 13/0213* (2013.01);
(Continued)

(58) Field of Classification Search
CPC ...... A61F 13/00012; A61F 2013/00463; A61F 2013/00468; A61F 2013/00472;
(Continued)

(56) References Cited

U.S. PATENT DOCUMENTS 2,507,244 A  5/1950 Correll
2,558,395 A  6/1951 Studer
(Continued)

FOREIGN PATENT DOCUMENTS

CO  6430437  4/2012
EP  0132983 A  2/1985
(Continued)

OTHER PUBLICATIONS

Nimni, M. E., et al., "Chemically modified collagen: A natural biomaterial for tissue replacement", J. Biomed. Mater. Res., Jun. 1987; 21(6), pp. 741-771.
(Continued)

*Primary Examiner* — Jacqueline Stephens
(74) *Attorney, Agent, or Firm* — K&L Gates LLP

(57) ABSTRACT

The present invention provides a hemostatic composite sponge comprising a porous matrix of a biomaterial and a bioadhesive material stably associated with said sponge and present in an organized pattern on said sponge.

20 Claims, 4 Drawing Sheets

Related U.S. Application Data continuation of application No. 12/970,203, filed on Dec. 16, 2010, now Pat. No. 8,771,258.

(60) Provisional application No. 61/287,088, filed on Dec. 16, 2009.

(51) Int. Cl.

| | |
|---|---|
| *A61F 13/15* | (2006.01) |
| *A61L 15/42* | (2006.01) |
| *A61L 15/58* | (2006.01) |
| *C08G 65/334* | (2006.01) |
| *C09J 171/02* | (2006.01) |
| *A61L 15/22* | (2006.01) |
| *A61F 13/02* | (2006.01) |
| *A61F 13/00* | (2006.01) |

(52) U.S. Cl.
CPC ...... *A61F 13/0253* (2013.01); *A61F 13/0289* (2013.01); *A61F 13/15577* (2013.01); *A61L 15/225* (2013.01); *A61L 15/58* (2013.01); *C08G 65/334* (2013.01); *C09J 171/02* (2013.01); *A61F 13/00012* (2013.01); *A61F 2013/00463* (2013.01); *A61F 2013/00468* (2013.01); *A61F 2013/00472* (2013.01); *A61L 2400/04* (2013.01); *C08L 2205/05* (2013.01)

(58) Field of Classification Search
CPC .............. A61F 13/0213; A61F 13/0253; A61F 13/0289; A61F 13/15577; A61L 15/425; A61L 15/225; A61L 15/58; C08G 65/334; C08J 171/02
USPC .................................. 604/540, 543, 367, 368
See application file for complete search history.

(56) References Cited

U.S. PATENT DOCUMENTS

| | | |
|---|---|---|
| 4,013,078 A | 3/1977 | Field |
| 4,124,705 A | 11/1978 | Rothman et al. |
| 4,164,559 A | 8/1979 | Miyata et al. |
| 4,179,400 A | 12/1979 | Tsao et al. |
| 4,265,233 A | 5/1981 | Sugitachi et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,424,208 A | 1/1984 | Wallace et al. |
| 4,453,939 A | 6/1984 | Zimmerman et al. |
| 4,482,386 A | 11/1984 | Wittwer et al. |
| 4,515,637 A | 5/1985 | Cioca |
| 4,536,387 A | 8/1985 | Sakamoto et al. |
| 4,540,410 A | 9/1985 | Wood et al. |
| 4,543,332 A | 9/1985 | Jao et al. |
| 4,554,156 A | 11/1985 | Fischer |
| 4,600,574 A | 7/1986 | Lindner et al. |
| 4,640,834 A | 2/1987 | Eibl et al. |
| 4,655,211 A | 4/1987 | Sakamoto et al. |
| 4,746,514 A | 5/1988 | Warne |
| 4,749,689 A | 6/1988 | Miyata et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,891,359 A | 1/1990 | Saferstein et al. |
| 4,925,677 A | 5/1990 | Feijen |
| 4,946,870 A | 8/1990 | Partain, III et al. |
| 5,007,916 A | 4/1991 | Linsky et al. |
| 5,017,229 A | 5/1991 | Burns et al. |
| 5,023,082 A | 6/1991 | Friedman et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro |
| 5,162,430 A | 11/1992 | Rhee et al. |
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,653,699 A * | 8/1997 | Reed ............. A61F 13/023 604/307 |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,853,749 A | 12/1998 | Hobbs |
| 5,874,500 A | 2/1999 | Rhee et al. |
| 5,902,832 A | 5/1999 | Van Bladel et al. |
| 5,908,054 A | 6/1999 | Safabash et al. |
| 5,931,165 A | 8/1999 | Reich et al. |
| 5,959,735 A | 9/1999 | Maris et al. |
| 5,997,895 A | 12/1999 | Narotam et al. |
| 6,063,061 A | 5/2000 | Wallace et al. |
| 6,066,325 A | 5/2000 | Wallace et al. |
| 6,110,484 A | 8/2000 | Sierra |
| 6,129,761 A | 10/2000 | Hubbell |
| 6,166,130 A | 12/2000 | Rhee et al. |
| 6,179,872 B1 | 1/2001 | Bell et al. |
| 6,277,394 B1 | 8/2001 | Sierra |
| 6,312,474 B1 | 11/2001 | Francis et al. |
| 6,312,725 B1 | 11/2001 | Wallace et al. |
| 6,328,229 B1 | 12/2001 | Duronio et al. |
| 6,458,386 B1 | 10/2002 | Schacht et al. |

(56) References Cited

U.S. PATENT DOCUMENTS

| | | |
|---|---|---|
| 6,458,889 B1 | 10/2002 | Trollsas |
| 6,495,127 B1 | 12/2002 | Wallace et al. |
| 6,624,245 B2 | 9/2003 | Wallace et al. |
| 6,706,690 B2 | 3/2004 | Reich et al. |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |
| 8,771,258 B2 | 7/2014 | Hedrich et al. |
| 2002/0193448 A1 | 12/2002 | Wallace et al. |
| 2003/0064109 A1 | 4/2003 | Qian et al. |
| 2006/0147492 A1 | 7/2006 | Hunter et al. |
| 2006/0167561 A1 | 7/2006 | Odar et al. |
| 2008/0085316 A1 | 4/2008 | Qian et al. |
| 2008/0091277 A1 | 4/2008 | Deutsch et al. |
| 2008/0187591 A1 | 8/2008 | Rhee et al. |
| 2008/0286376 A1 | 11/2008 | Qian et al. |
| 2009/0142396 A1 | 6/2009 | Odar et al. |
| 2010/0028309 A1 | 2/2010 | Odar et al. |
| 2010/0100123 A1 | 4/2010 | Bennett |
| 2010/0292717 A1 | 11/2010 | Petter-Puchner et al. |
| 2010/0316719 A1 | 12/2010 | Nagasaki et al. |
| 2010/0318048 A1 | 12/2010 | Hoeffinghoff et al. |
| 2011/0202026 A1 | 8/2011 | Hedrich et al. |
| 2011/0251574 A1 | 10/2011 | Hedrich et al. |

FOREIGN PATENT DOCUMENTS

| | | |
|---|---|---|
| EP | 0376931 | 7/1990 |
| EP | 0132983 B1 | 12/1991 |
| EP | 0493387 | 7/1992 |
| EP | 0891193 | 1/1999 |
| EP | 0612252 | 5/1999 |
| EP | 1084720 | 3/2001 |
| EP | 1283063 | 2/2003 |
| EP | 1484070 | 12/2004 |
| EP | 1414370 | 4/2007 |
| JP | 59-113889 | 6/1984 |
| JP | 05308969 | 11/1993 |
| JP | 6-254148 | 9/1994 |
| JP | 9-504719 | 5/1997 |
| JP | 2000510357 | 8/2000 |
| JP | 2002526207 | 8/2002 |
| JP | 2003535165 | 11/2003 |
| JP | 2007001963 | 1/2007 |
| JP | 07090241 | 4/2007 |
| JP | 2008220388 | 9/2008 |
| KR | 10-1991-0007847 | 10/1991 |
| WO | 9013320 | 11/1990 |
| WO | 9221354 | 12/1992 |
| WO | 9222252 | 12/1992 |
| WO | 9427630 | 12/1994 |
| WO | 9844963 | 10/1998 |
| WO | 200222184 | 3/2002 |
| WO | 2002070594 | 9/2002 |
| WO | 2003007845 | 1/2003 |
| WO | 2004108179 | 12/2004 |
| WO | 2006031358 | 3/2006 |
| WO | 2007001926 | 1/2007 |
| WO | 2007137839 | 12/2007 |
| WO | 2008016983 | 2/2008 |

OTHER PUBLICATIONS

Nimni, Marcel E., "The cross-linking and structure modification of the collagen matrix in the design of cardiovascular prosthesis", J. of Cardiac Surgery, Dec. 1988;3(4), pp. 523-533.
O'Neill, P., et al.; "Use of Porcine Dermis as Dural Substitute in 72 Patients"; J. Neurosurg.; vol. 61;pp. 351-354 (Aug. 1984).
Palm, S.J., et al.; "Dural Closure with Nonpenetrating Clips Prevents Meningoneural Adhesions: An Experimental Study in Dogs"; Neurosurgery; vol. 45:4; pp. 875-882 (Oct. 1999).
Parizek, J., et al.; "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery"; Acta Neurochir; vol. 139; pp. 827-838 (1997).
Park, Y-K., at al.; "Prevention of Arachnoiditis and Postoperative Tethering of the Spinal Cord with Gore-Tex Surgical Membrane: An Experimental Study with Rats"; Neurosurgery; vol. 42 :4; pp. 813-824 (Apr. 1998).
PCT International Preliminary Report on Patentability dated Feb. 17, 2009 and Written Opinion and International Search Report dated Feb. 17, 2009, for International Application No. PCT/US2007/074984, 21 pages.
Pietrucha, K.; "New Collagen Implant as Dural Substitute"; Biomatarials; vol. 12; pp. 320-323 (Apr. 1991).
Pitt et al., "Controlled Release of Bioactive Materials", R. Baker, Ed., Academic Press, New York, 1980.
Porchet, Francois, "Inhibition of Epidural Fibrosis with ADCON-L: Effect on Clinical Outcome One Year Following Re-operation for Recurrent Lumbar Radiculopathy", 1998, pp. 1-10.
Raul, J.S., et al.; "Utilisation du Polyester Urethane (NEUROPATCH®) Comme Substitut Dural," Neurochirugie; vol. 49:2-3; pp. 83-89 (2003), English abstract only on p. 83.
Reddy, M., et al.; "A Clinical Study of a Fibrinogen-Based Collagen Fleece for Dural Repair in Neurosurgery"; Acta Neurochir; vol. 144; pp. 265-269 (2002).
Riley et al., "Percutaneous Liver Biopsy with Plugging of Needle Track: A Safe Method for Use in Patients with Impaired Coagulation", The Lancet (Aug. 25, 1984) pp. 436.
Rosenblatt, Joel, et al., "Effect of electrostatic forces on the dynamic rheological properties of injectable collagen biomaterials", Biomaterials, 1992; 13(12), pp. 878-886.
Rosenblatt, Joel, et al., "Injectable collagen as a pH-sensitive hydrogel", Biomaterials, Oct. 1994; 15(12), pp. 985-995.
Ross, Jeffrey S. et al., "Association Between Peridural Scar and Recurrent Radicular PAIN After Lumbar Discectomy: Magnetic Resonance Evaluation", Neurosurgery, pp. 855-863, 1996.
Rossler, B., et al., "Collagen microparticles: preparation and properties", J. Microencapsulation, Jan.-Feb. 1995;12(1), pp. 49-57.
San-Galli, F., et al.; "Experimental Evaluation of a Collagen-Coated Vicryl Mesh as a Dural Substitute"; Neurosurgery: vol. 30:3; pp. 396-401 (1992).
Shaffrey, C. I., et al.; "Neurosurgical Applications of Fibrin Glue: Augmentation of Dural Closure in 134 Patients"; Neurosurgery; vol. 26:2; pp. 207-210 (1990).
Sidman et al., "Biodegradable, Implantable Sustained Release Systems Based on Glutamic Acid Copolymers" J. Membrane Science (1979) 7:227-291.
Smith, KA, et al.; "Delayed Postoperative Tethering of the Cervical Spinal Corei"; J Neurosurg; vol. 81; pp. 196-201 (Aug. 1994).
Springorum, H.W.; "Die Verwendung von Kollagenfolien zur Uberbruckung von Defekten des Gleitgewebes bei Achillotenotomien und Achillessehnenrupturen"; Akt. Traumatal.; vol. 15; pp. 120-121 (1985), English abstract only on p. 120.
Sugitachi et al., "A Newly Devised Chemo-embolic Agent, G.T. XIII-ADM." (English abstract posted at http://www.ncbi.nlm.nih.gov/ on Jan. 3, 2001 from) Gan. To. Kagaku Ryoho. (1985) 12(10) 1942-1943.
Sugitachi et al., "Locoregional Therapy in Patients with Maignant Pleural Effusion—Two Different Kinds of BAG Therapy" (English abstract posted at http://www.ncbi.nlm.nih.gov/ on Jan. 3, 2001 from) Gan. To. Kagaku Ryoho. (1992) 19(10):1640-1643.
Sugitachi et al., "Preoperative Transcatheter Arterial Chemoembolization for Locally Advanced Breast Cancer: Application for New Thrombotic Materials" Japan J. Surg. (1983) 13(5):456-458.
Tobin et al., "Plugged Liver Biopsy in Patients with Impaired Coagulation", Digestive Diseases and Science (1989) 34(1):13-15.
Tucker et al., "Absorbable Gelatin (Gelfoam) Sponge" Charles T. Thomas, Publisher, Springfield, Illinois, 3-125. 1965.
Vander Salm et al., "Reduction of Sternal Infection by Application of Topical Vancomycin" J. Thorac. Surg. (1989) 98:618-622.
Vinas, F.E., et al.; "Evaluation of Expanded Polytetrafluoroethylene (ePTFE) versus Polydioxanone (PDS) for the Repair of Dura Mater Defects"; Neurological Research; vol. 21; pp. 262-268 (Apr. 1999).

(56) References Cited

OTHER PUBLICATIONS

Wallace, Donald G., et al., "Injectable cross-linked collagen with improved flow properties", J. of Biomedical Materials Research, Aug. 1989; 23(8), pp. 931-945.
Wallace, Donald, "The relative contribution of electrostatic interactions to stabilization of collagen fibrils", Biopolymers, May-Jun. 1990; 29(6-7), pp. 1015-1026.
Warren, W.L., et al.; Dural Repair Using Acellular Human Dermis: Experience with 200 Cases: Technique Assessment; Neurosurgery; Vol. 46:6; pp. 1391-1396 (Jun. 2000).
Yuki et al., "Effects of Endoscopic Variceal Sclerotherapy using GT XIII on Blood Coagulation Tests and the Renal Kallikrein-kinin System" (English abstract posted at http://www.ncbi.nlm.nih.gov/ on Jan. 3, 2001 from) Gastroentral. Japan (1990) 25(5):561-567.
Ziegelaar, B.W. et al., "The characterisation of human respiratory epithelial cells cultured on reabsorbable scaffolds: first steps towards a tissue engineered tracheal replacement", Biomaterials 23 (2002), 1425-1438; ISSN 0142-9612.
Ziegelaar, B.W.; "Tissue Engineering of a Tracheal Equivalent", Doctoral Thesis at Ludwig Maximilians University, Munich, Germany; 25 pages (2004).
Zins et al., "US-Guided Percutaneous Liver Biopsy with Plugging of the Needle Track: A Prospective Study in 72 High-Rish Patients" Radiology (1992) 184(3):841-843.
Ansell et al., "Gelfoam and Autologous Clot Embolization: Effect on Coagulation", Invest. Radio/. (1978) 13:115-120.
Barrow, D.L., et al.; "The Use of Greater Omentum Vascularized Free Flaps for Neurosurgical Disorders Requiring Reconstruction"; J. Neurosurg.; vol. 60; pp. 305-311 (Feb. 1984).
Barton et al., "Fibrin Glue as a Biologic Vascular Patch—A Comparative Study" (abstract posted at http://www.ncbi.nlm.nih.gov/ on Jan. 3, 2001 from) J. Surg. Res. (1986) 40(5): 510-513.
Baxter product brochure for TissuFleece E, TissuCone E and TissuFoil E (2003).
Baxter Product Catalogue; Collagen; 4 pages (2006).
Baxter, "GentaFleece Collagen Fleece—Version 5: Collagen Sponge with antibiotic protection for surgical use," Retrieved from http://www.advancingbiosurgery.com/en_EU/downloads/ifu_gentafleece.pdf, Mar. 2002, 2 pages. English portion second column of first page.
Boyers et al., "Reduction of Postoperative Pelvic Adhesions in the Rabbit with Gore-Tex Surgical Membrane" Fert. Ster. (1988) 49(6): 1066-1070.
Bruck, S. D., Ed., "Controlled Drug Delivery", CRC Press, Boca Raton, FL (1983) A title page and table of contents.
Cantor et al., "Gelfoam and Thrombin in Gastrointestinal Bleeding: An Experimental Study." Journal of Laboratory and Clinical Medicine vol. 35, No. 6 (1950): pp. 890-893.
Cantor et al., "Gelfoam and Thrombin in Treatment of Massive Gastroduodenal Hemmorhage: A Preliminary Report" Am J. Surg. (1950) pp. 883-887.
Cantor et al., "Gelfoam and Thrombin in Treatment of Massive Upper Gastroduodenal Hemorrhage", Am. J. Surg. (1951) pp. 230-235.
Chaplin, J.M., et al.; "Use of an Acellular Dermal Allograft for Dural Replacement: An Experimental Study"; Neurosurgery: Vol. 45:2; pp. 320-327 (Aug. 1999).
Cheung, David T., et al., "Mechanism of crosslinking of proteins by glutaraldehyde IV: In Vitro and In Vivo stability of a crosslinked collagen matrix", Connective Tissue Research, 1990;25(1), pp. 27-34.
Christensen, et al., "Qualitative Description of the Wurster-Based Fluid-Bed Coating Process." Drug Development and Industrial Pharmacy, vol. 23, No. 5, pp. 451-463, 1997.
Collins et al., "Enemata of Gelfoam-Milk Suspension Combined with Thrombin Solution to Control Massive Hemorrhage Following Anorectal Surgery", Am. J. Proctol. (1951) 2:60-63.
Collins, Ronald et al., "Use of Collagen Film as a Dural Substitute: Preliminary Animal Studies", Journal of Biomedical Materials Research vol. 25, 267-276 (1991).

Edgerton et al., "Vascular Hamartomas and Hemangiomas: Classification and Treatment" Southern Med. J. (1982) 75(12):1541-1547.
Filippi, R., et al.; "Bovine Pericardium for Duraplasty: Clinical Results in 32 Patients"; Neurosurg. Rev.; vol. 20; pp. 103-107 (2001).
Heller et al., "Release of Norethindrone from Poly(Ortho Esters)" Polymer Engineering Sci. (1981) 21:727-731.
Hieb, Lee D. et al., "Spontaneous Postoperative Cerebrospinal Fluid Leaks Following Application of Anti-Adhesion Barrier Gel", Spine vol. 26, No. 7, pp. 748-751, 2001.
Hood et al., "Efficacy of Topical Hemostat Floseal Matrix in Vascular Surgery," 24th World Congress of the International Society for Cardiovascular Surgery (Sep. 12-16, 1999), 2 pages total.
Hotz et al., "Collagen and Fibrin as Biologic Binders from Granular Hydroxyapatite" (abstract posted at http://www.ncbi.nlm.nih.gov/ on Jan. 3, 2001 from) Dtsh. Z. Mund. Kiefer Geichtshir. (1989) 13(4):296-300.
Jeong et al., "Biodegradable Block Copolymers as Injectible Drug-Delivery Systems" Nature (1997) 388:860-862.
Jonas, Richard A., et al., "A new sealant for knitted Dacron prostheses: Minimally cross-linked gelatin", J. Vase. Surg., Mar. 1988;7(3), pp. 414-419.
Kim, Kee D., et al., "Reduction in Leg Pain and Lower-Extremity Weakness with Oxiplex/SP Gel for 1 Year after Laminactomy, Laminotomy, and Disectomy", Neurosurg Focus 17 (1): Clinical Pearl 1, Jul. 2004, pp. 1-6.
Kline, D. G.; "Dural Replacement with Resorbable Collagen"; Arch Surg; vol. 91; pp. 924-929 (Dec. 1965).
Knopp, U., "A new collagen foil versus a cadaveric dura graft for dural defects—a comparative animal experimental study", EANS—12th European Congress of Neurosurgery, Lisbon, Sep. 7-12, 2003, 663-666.
Kofidis, T., et al., "Clinically established Hemostatis Scaffold (Tissue Fleece) as Biomatrix in Tissue and organ-engineering research", Tissue Eng vol. 9, No. 3, 2003, S.517-523; ISSN: 1076-3279.
Krill et al., "Topical Thrombin and Powdered Gelfoam: An Efficient Hemostatic Treatment for Surgery", J. Tenn. Dent. Assoc. (1986) 66(2):26-27.
Kuhn, J. et al., "Bilateral Subdural Haematomata and Lumbar Pseudomeningocele Due to a Chronic Leakage of Liquor Cerebrospinalis after a Lumbar Disectomy with the Application of ADCON-L Gel", J. Neural Neurosurg. Psychiarty 2005; 76: 1031-1033.
Langer et al., "Chemical and Physical Structure of Polymerns as Carriers for Controlled Release of Bioactive Agents: A Review" Rev. Marco Chem. Phys. (1983) C23(1):61-126.
Laquerriere, A., et al.; "Experimental Evaluation of Bilayered Human Collagen as a Dural Substitute"; J. Neurosurg; vol. 78; pp. 487-491 (Mar. 1993).
Larson, Paul O., "Topical Hemostatic Agents for Dermatologic Surgery", J. Dermatol. Surg. Oneal., Jun. 1988;14(6), pp. 623-632.
Le, Anh X. et al., "Unrecognized Durotomy After Lumbar Discectomy: A Report of Four Cases Associated with the Use of ADCON-L", Spine vol. 26, No. 1, pp. 115-118, 2001.
Lee, J.F. et al.; "Experimental Evaluation of Silicone-Coated Dacron and Collagen Fabric-Film Laminate as Dural Substitutes"; J. Neurosurg.; vol. 27; pp. 558-564 (Apr. 1967).
Leong et al., "Polyanhydrides for Controlled Release of Bioactive Agents" Biomaterials (1986) 7:364-371.
Leong et al., "Polymeric Controlled Drug Delivery" Adv. Drug Delivery Rev. (1987)1:199-233.
Maok, "Hemostatic Agents" (1991) Today's O.R. Nurse, pp. 6-10.
Masar et al., "Synthesis of Polyurethanes and Investigation of their Hydrolytic Stability", J. Polymer. Sci., Polymer Symposium (1979) 66:259-268.
Matsumoto, K., et al.; "A Gelatin Coated Collagen-Polyglycolic Acid Composite Membrane as a Dural Substitute"; ASAIO Journal; pp. 641-645 (2001).
Maurer, P.K., et al.; "Vicryl (Polyglactin 910) Mesh as a Dural Substitute"; J Neurosurg; vol. 63; pp. 448-452 (Sep. 1985).

(56) References Cited

OTHER PUBLICATIONS

McClure et al., "Massive Gastroduodenal Hemorrhage: Treatment with Powdered Gelfoam and Buffered Thrombin Solution" Surg. (1952) 32:630-637.
McPherson, J. M. et al., "An examination of the biologic response to injectable, glutaraldehyde cross-linked collagen implants", J. Biomed. Mater. Res., Jan. 1986;20(1), pp. 93-107.
McPherson, J. M., et al., "The preparation and physiochemical characterization of an injectable form of reconstituted, glutaraldehyde cross-linked, bovine corium collagen", J. Biomed. Mater. Res., Jan. 1986;20(1), pp. 79-92.
McPherson, John M., et al., "The Effects of Heparin on the Physiochemical Properties of Reconstituted Collagen", Co//. Relat. Res., Jan. 1988;8(1), pp. 65-82.
Meddings, N., et al.; "Collagen Vicryl—A New Dural Prosthesis"; Acta Neurochir, vol. 117; pp. 53-58 (1992).
Mello, L.R., et al.; "Duraplasty with Biosynthetic Cellulose: An Experimental Study"; J Neurosurg; vol. 86; pp. 143-150 (Jan. 1997).
Narotam, P.K., et al.; "A Clinicopathological Study of Collagen Sponge as a Dural Graft in Neurosurgery"; J Neurosurg; vol. 82; pp. 406-412 (Mar. 1995).
Narotam, P.K., et al.; "Experimental Evaluation of Collagen Sponge as a Dural Graft"; British Journal of Neurosurgery; vol. 7; pp. 635-641 (1993).
Nimni, M. E., et al., "Chemically modified collagen: A natural biomaterial for tissue replacement", J. Biomed. Mater. Res., Jun. 1987;21(6), pp. 741-771.

\* cited by examiner

HEMOSTATIC SPONGE

CROSS REFERENCE TO RELATED APPLICATIONS

This application is a continuation of U.S. application Ser. No. 14/320,064, filed Jun. 30, 2014, and now patented as U.S. Pat. No. 9,517,287, which is a continuation of U.S. patent application Ser. No. 12/970,203, filed Dec. 16, 2010, and now patented as U.S. Pat. No. 8,771,258, which is a nonprovisional of, and claims the benefit of priority to, U.S. Provisional Application No. 61/287,088, filed Dec. 16, 2009, the entire contents of which are incorporated herein by reference for all purposes.

FIELD OF THE INVENTION

The present invention relates to the field of hemostatic sponges, a method of producing said sponges and their uses in hemostasis.

BACKGROUND OF THE INVENTION

Biological glues based on coagulation factors of human or animal origin have long been known. A method for producing tissue adhesives based on fibrinogen and factor XIII has been described in U.S. Pat. No. 4,362,567, U.S. Pat. No. 4,298,598 and U.S. Pat. No. 4,377,572. The tissue adhesives are usually applied together with a separate component containing thrombin, which is enzymatically acting on fibrinogen to form fibrin, and on factor XIII to form the active factor XIIIa, which cross-links the fibrin to obtain a stable fibrin clot.

Collagen pads have been used for many years to improve wound healing or to stop bleeding. Their mechanism of action in hemostasis is based on platelet aggregation and activation, the formation of thrombin on the surface of activated platelets and the formation of a hemostatic fibrin clot by the catalytic action of thrombin on fibrinogen. To improve the hemostatic action of collagen pads or sheets it has been suggested to include factors of hemostasis within such pads.

In U.S. Pat. No. 4,600,574 a tissue adhesive based on collagen combined with fibrinogen and factor XIII is described. This material is provided in the lyophilized form, ready for use. The fibrinogen and factor XIII are combined with the collagen by impregnating the collagenous flat material with a solution comprising fibrinogen and factor XIII, and lyophilizing said material.

The WO 97/37694 discloses a hemostatic sponge based on collagen and an activator or proactivator of blood coagulation homogeneously distributed therein. This sponge is provided in a dry form, which could be air-dried or lyophilized. However, it still contains a water content of at least 2%.

U.S. Pat. No. 5,614,587 discusses bioadhesive compositions comprising cross-linked collagen using a multifunctionally activated synthetic hydrophilic polymer, as well as methods of using such compositions to effect adhesion between a first surface and a second surface, wherein at least one of the first and second surfaces can be a native tissue surface.

Collagen-containing compositions which have been mechanically disrupted to alter their physical properties are described in U.S. Pat. No. 5,428,024, U.S. Pat. No. 5,352,715, and U.S. Pat. No. 5,204,382. These patents generally relate to fibrillar and insoluble collagens. An injectable collagen composition is described in U.S. Pat. No. 4,803,075. An injectable bone/cartilage composition is described in U.S. Pat. No. 5,516,532. A collagen-based delivery matrix comprising dry particles in the size range from µm to 850 µm which may be suspended in water and which has a particular surface charge density is described in WO 96/39159. A collagen preparation having a particle size from 1 µm to 50 µm useful as an aerosol spray to form a wound dressing is described in U.S. Pat. No. 5,196,185. Other patents describing collagen compositions include U.S. Pat. No. 5,672,336 and U.S. Pat. No. 5,356,614.

BRIEF SUMMARY OF THE INVENTION

The subject of the invention is a hemostatic porous composite sponge comprising a matrix of a biomaterial and a material enhancing the adherence of said sponge to the applied tissue stably associated with at least one surface of said sponge, wherein said material is essentially free of a hydrogel forming component.

It has been found that previous pads of fibrous biomaterials, in particular collagen pads, for wound healing failed to induce hemostasis at conditions with impaired hemostasis (e.g. after heparinization). The inventive sponge improves hemostasis.

It has further been found that if a further material is present on a surface of the biomatrix material as an active hemostatic layer such a layer tends to be instable in that the material has a tendency to detach from the sponge, especially during application of the sponge on the tissue and when being adjusted to the geometry of said tissue.

It has also been found that the absence of a further hydrogel forming component, such as e.g. a particulate material, e.g. gelatin particles, has advantageous properties especially with regard to lower swelling properties of the sponge as a whole.

It has been possible to overcome these drawbacks in that a sponge of the present invention is provided.

A further aspect relates to a method of manufacturing a hemostatic porous sponge comprising
  a) providing a porous sponge of a matrix of a bio material,
  b) providing a material enhancing the adherence of said sponge to the applied tissue in the form of a suspension, a solution or powder, wherein said material is essentially free of a hydrogel forming component,
  c) contacting a) and b) so that the material of b) is stably associated with at least one surface of said sponge so that a hemostatic composite sponge is obtained, optionally
  d) drying the composite sponge obtained in step c), optionally
  e) sterilizing said composite sponge obtained in step c) or d).

Another aspect relates to a method of treating an injury comprising administering a hemostatic porous composite sponge to the site of injury.

Also provided is a kit for preparing a wound coverage, comprising a sponge as herein disclosed and pharmaceutically active substances. This kit and its components are in particular for the manufacture of a medical sponge for the treatment of an injury.

Those skilled in the art will readily understand that all preferred embodiments disclosed in the following are examples of specific embodiments, but are not necessarily limiting the general inventive concept. Furthermore, all special embodiments can be read on all inventive aspects and embodiments in any combination, if not mutually exclusive. All equivalents or obvious alterations or modifications as recognized by those skilled in the art are included by the present invention.

Figure 1:
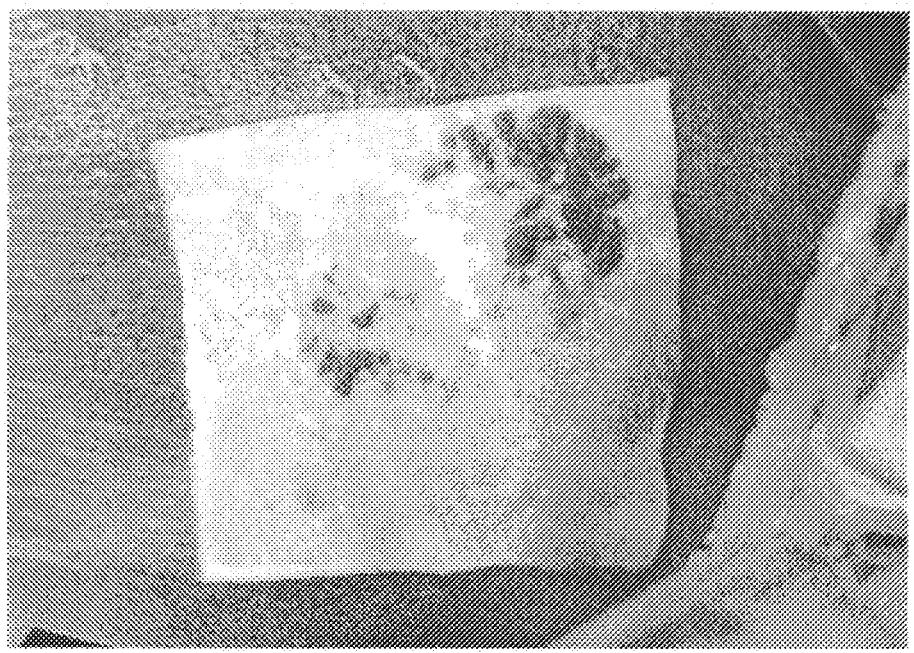
FIGS. 1 to 4 show hemostatic performances of the sponges prepared according to examples 1 (=FIG. 1), 4 (=FIG. 2), 5 (=FIG. 3) and 6 (=FIG. 4) in an animal model as described in Example 10.

The present invention is further exemplified by the following examples without being limited thereto.

The following abbreviations are used:
COH102 Pentaerythritolpoly(ethyleneglycol)ether tetra-succinimidyl glutarate
COH206 Pentaerythritolpoly(ethyleneglycol)ether tetra-thiol
EtOH ethanol
PEG polyethylene glycol
PET polyethylene terephthalate.

DETAILED DESCRIPTION OF THE INVENTION

The object of the invention is a hemostatic porous composite sponge comprising a matrix of a biomaterial and a material enhancing the adherence of said sponge to the applied tissue stably associated with at least one surface of said sponge, wherein said material is essentially free of a hydrogel forming component.

"Stably associated" according to the present invention means that the material enhancing the adherence of said sponge to the applied tissue stays firmly associated with the sponge during application of this sponge to the tissue and adjusting to the geometry of said tissue, even if the sponge is e.g. bended during that application.

Preferably the biomaterial is collagen, a protein, a biopolymer, or a polysaccharide. Especially preferred is a biomaterial selected from the group consisting of collagen, gelatin, fibrin, a polysaccharide, e.g. chitosan, and a derivative thereof, more preferred collagen and chitosan, especially preferred collagen.

The sponge is a porous network of a biomaterial able to absorb body fluids when applied to the site of an injury. Furthermore, the sponge is usually flexible and suitable to be applied on diverse tissues and locations with various shapes.

The collagen used for the present invention can be from any collagen suitable to form a gel, including a material from liquid, pasty, fibrous or powdery collageneous materials that can be processed to a porous or fibrous matrix. The preparation of a collagen gel for the production of a sponge is e.g. described in the EP 0891193 (incorporated herein by reference) and may include acidification until gel formation occurs and subsequent pH neutralisation. To improve gel forming capabilities or solubility the collagen may be (partially) hydrolyzed or modified, as long as the property to form a stable sponge when dried is not diminished.

The collagen sponge according to the present invention preferably has a lower density as compared to the density of a collagen film. Preferably the density is between about 5 to about 100 mg per cm3, whereas densities of films are higher than about 650 mg per cm3. An especially preferred collagen sponge according to the present invention is the one marketed under the name Matristypt®.

The collagen or gelatin of the sponge matrix is preferably of animal origin, preferably bovine or equine. However, also human collagen might be used in case of a hypersensitivity of the patient towards xenogenic proteins. The further components of the sponge are preferably of human origin, which makes the sponge suitable especially for the application to a human.

In a preferred embodiment the matrix material of the fibrous biocompatible polymer which forms the porous network of the sponge constitutes of between 1-50%, 1-10%, preferably about 3% of the dried porous sponge (w/w-%).

In a preferred embodiment the material enhancing the adherence of said sponge to the applied tissue, in the following called "the material", is a mixture of two pre-polymers comprising a first cross-linkable component and a second cross-linkable component that cross-links with the first cross-linkable component under reaction enabling conditions or a formed polymer in association with said sponge.

The material enhancing the adherence of said sponge to the applied tissue stably associated with at least one surface of said sponge is essentially free of a hydrogel forming component, especially free of a particulate hydrogel forming component, e.g. gelatin particulate material or gelatin particles.

More preferably said first and/or second cross-linkable component comprise a derivative of polyethylene glycol (PEG), e.g. a derivative which is able to react under given conditions. Preferably one of the cross-linkable components is capable of covalently reacting with tissue.

Such materials suitable for a sponge for use as a hemostat are e.g. disclosed in the WO2008/016983 (incorporated herein by reference in its entirety) and commercially available under the trademark CoSeal®. Preferred materials mediate adjunctive hemostasis by themselves, and can be suitable to mechanically seal areas of leakage. Such materials are for ex-ample bioresorbable polymers, in particular polymers that cross-link and solidify upon exposure to body fluids. In further embodiments the material is resorbable and/or biocompatible and can be degraded by a subject, in particular a human subject, in less than 6 months, less than 3 months, less than 1 month or less than 2 weeks.

A special material enhancing the adherence of said sponge to the applied tissue may comprise a first cross-linkable component, a second cross-linkable component that cross-links with the first cross-linkable component under reaction enabling conditions, wherein the first and second cross-linkable component cross-link to form a layer.

The first cross-linkable component can include multiple nucleophilic groups and the second cross-linkable component can include multiple electrophilic groups. Upon contact with a biological fluid, or in other reaction enabling conditions, the cross-linkable first and second components cross-link to form a porous matrix having interstices.

In some aspects, the first cross-linkable component of the material includes a multi-nucleophilic polyalkylene oxide having m nucleophilic groups, and the second cross-linkable component includes a multi-electrophilic polyalkylene oxide. The multi-nucleophilic polyalkylene oxide can include two or more nucleophilic groups, for example $NH_2$, —SH, —H, —$PH_2$, and/or —CO—NH—$NH_2$. In some cases, the multi-nucleophilic polyalkylene oxide includes two or more primary amino groups. In some cases, the multi-nucleophilic polyalkylene oxide includes two or more thiol groups. The multi-nucleophilic polyalkylene oxide can be polyethylene glycol or a derivative thereof. In some cases, the polyethylene glycol includes two or more nucleophilic groups, which may include a primary amino group and/or a thiol group. The multi-electrophilic polyalkylene oxide can include two or more electrophilic groups such as CO2N(COCH2) 2, —CO2H, —CHO, —CHOCH2, —N═C═O, —SO2CH═CH2, N(COCH) 2, and/or —S—S—(C5H4N). The multi-electrophilic olyalkylene oxide may include two or more succinimidyl groups. The multi-electrophilic polyalkylene oxide may include two or more maleimidyl groups. In some cases, the multi-electrophilic polyalkylene oxide can be a polyethylene glycol or a derivative thereof.

In special embodiments the first and/or second cross-linkable component is/are synthetic polymers, preferably comprising PEG. The polymer can be a derivative of PEG comprising active side groups suitable for cross-linking and adherence to a tissue. Preferably, the adhesive comprises succinimidyl, maleimidyl and/or thiol groups. In a two polymer set-up, one polymer may have succinyl or maleimidyl groups and a second polymer may have thiol or amino groups which can attach to the groups of the first polymer. These or additional groups of the adhesive may facilitate the adherence to a tissue.

Preferably the material enhancing the adherence of said sponge to the applied tissue, such as modified PEG materials as mentioned before, is present in a range of 5 to 50 mg/cm2 of the biomaterial, preferably 10 to 20 mg/cm2 of the biomaterial, e.g. collagen.

The sponge as a whole is biodegradable, being suitable for biological decomposition in vivo, or bioresorbable, i.e. able to be resorbed in vivo. Full resorption means that no significant extracellular fragments remain. A biodegradable material differs from a non-biodegradable material in that a biodegradable material can be biologically decomposed into units which may either be removed from the biological system and/or chemically incorporated into the biological system. In a preferred embodiment the particular material, the matrix material or sponge as a whole can be degraded by a subject, in particular a human subject, in less than 6 month, less than 3 month, less than 1 month, less than 2 weeks.

In a preferred embodiment the sponge has the material enhancing the adherence of said sponge to the applied tissue in the form of a continuous or discontinuous layer on at least one surface of said sponge.

The sponge of the present invention preferably has an overall thickness of less than 2.5 mm, more preferred about 1 mm to about 2.5 mm.

The sponge of the present invention is preferably used in minimal invasive surgery, e.g. for laparoscopic application.

The sponge may be dried and after drying, the sponge may have a water content of at least 0.5 (percentages given in w/w here). In certain embodiments the sponge can be freeze-dried or air-dried.

The sponge may further comprise an activator or proactivator of blood coagulation, including fibrinogen, thrombin or a thrombin precursor, as e.g. disclosed in U.S. Pat. No. 5,714,370 (incorporated herein by reference). Thrombin or the precursor of thrombin is understood as a protein that has thrombin activity and that induces thrombin activity when it is contacted with blood or after application to the patient, respectively. Its activity is expressed as thrombin activity (NIH—Unit) or thrombin equivalent activity developing the corresponding NIH-Unit. The activity in the sponge can be 100-10.000, preferably 500-5.000. In the following thrombin activity is understood to comprise both, the activity of thrombin or any equivalent activity. A protein with thrombin activity might be selected from the group consisting of alpha-thrombin, meizothrombin, a thrombin derivative or a recombinant thrombin. A suitable precursor is possibly selected from the group consisting of: prothrombin, factor Xa optionally together with phospholipids, factor IXa, activated prothrombin complex, FEIBA, any activator or a proactivator of the intrinsic or extrinsic coagulation, or mixtures thereof.

The hemostatic sponge according to the invention might be used together with further physiologic substances. For example, the sponge preferably further comprises pharmacologically active substances, among them antifibrinolytics, such as a plasminogenactivator-inhibitor or a plasmin inhibitor or an inactivator of fibrinolytics. A preferred antifibrinolytic is selected from the group consisting of aprotinin or an aprotinin derivative, alpha2-macroglobulin, an inhibitor or inactivator of protein C or activated protein C, a substrate mimic binding to plasmin that acts competitively with natural substrates, and an antibody inhibiting fibrinolytic activity.

As a further pharmacologically active substance an antibiotic, such as an antibacterial or antimycotic might be used together with the sponge according to the invention, preferably as a component homogeneously distributed in the sponge. Further bioactive substances such as growth factors and/or pain killers may be also present in the inventive sponge. Such a sponge might be useful in e.g. wound healing. Further combinations are preferred with specific enzymes or enzyme inhibitors, which may regulate, i.e. accelerate or inhibit, the resorption of the sponge. Among those are collagenase, its enhancers or inhibitors. Also, a suitable preservative may be used together with the sponge or may be contained in the sponge.

Although a preferred embodiment relates to the use of the hemostatic sponge which contains the activator or proactivator of blood coagulation as the only active component, further substances that influence the velocity of blood coagulation, hemostasis and quality of the sealing, such as tensile strength, inner (adhesive) strength and durability might be comprised.

Procoagulants that enhance or improve the intrinsic or extrinsic coagulation, such as factors or cofactors of blood coagulation, factor XIII, tissue factor, prothrombin complex, activated prothrombin complex, or parts of the complexes, a prothrombinase complex, phospholipids and calcium ions, might be used. In case of a surgical procedure where a precise sealing is needed, it might be preferable to prolong the working period after the hemostatic sponge is applied to the patient and before clotting is affected. The prolongation of the clotting reaction will be ensured, if the sponge according to the invention further comprises inhibitors of blood coagulation in appropriate amounts. Inhibitors, such as antithrombin III optionally together with heparin, or any other serine protease inhibitor, are preferred.

It is also preferred to have such additives, in particular the thrombin or a precursor of thrombin evenly distributed in the material in order to prevent local instability or hypercoagulability of the material. Even with a certain water content the thrombin activity is surprisingly stable, probably because of the intimate contact of thrombin and collagen in the homogeneous mixture. Nevertheless, thrombin stabilizers preferably selected from the group consisting of a polyol, a polysaccharide, a polyalkylene glycol, amino acids or mixtures thereof might be used according to the invention. The exemplary use of sorbitol, glycerol, polyethylene glycol, polypropylene glycol, mono- or disaccharides such as glucose or saccharose or any sugar or sulfonated amino acid capable of stabilizing thrombin activity is preferred.

In another embodiment a biocompatible, resorbable hydrogel capable of absorbing liquid is contained within the sponge of the present invention.

The present invention also provides a wound coverage comprising a sponge according to the invention. The sponge and all additional layers can be provided in a ready to use wound coverage in suitable dimensions. The sponge and/or the coverage can be a pad or a sheet, preferably having a thickness of at least 3 mm or at least 5 mm and/or up to 20 mm, depending on the indication. When the relatively thick flexible sponge is applied to a wound it is important that blood and fibrinogen can be absorbed throughout the sponge before fibrin is formed that might act as a barrier for the absorption of further wound secret.

Another aspect of the invention relates to a method of manufacturing a hemostatic porous sponge comprising a) providing a sponge comprising a matrix of a biomaterial, b) providing a material enhancing the adherence of said sponge to the applied tissue in the form of a suspension, a solution or powder, c) contacting a) and b) so that the material of b) is present on at least one surface of said sponge, and optionally d) drying the sponge obtained in step c).

Drying may include freeze drying or air drying and comprises removing volatile components of the fluid.

In a further aspect the present invention provides a hemostatic porous sponge obtainable by the method according to the invention described above. All preferred embodiments mentioned above for a hemostatic sponge can also be read to this obtainable sponge.

The present invention also provides a method of treating an injury comprising administering a hemostatic porous composite sponge comprising a matrix of a biomaterial and a material enhancing the adherence of said sponge to the applied tissue. The injury may comprise a wound, a hemorrhage, damaged tissue and/or bleeding tissue.

EXAMPLES

Example 1: Collagen Sponges Treated with Acidic Solution of Two Reactive PEGs

Aqueous, acidic solutions (pH 3.0, HCl) of COH102 and COH206 with PEG-concentrations (COH102 and COH206 1:1) of 10 mg/cm$^3$, 35 mg/cm$^3$, 70 mg/cm$^3$ and 100 mg/cm$^3$ are prepared and filled into 9×7 cm PET-trays. Commercial available bovine collagen sponges (Matristypt®), 9×7 cm, with the same volume as the previously filled PEG-solution are placed on the top of the solutions. After absorption of the PEG-solution, the collagen materials are lyophilized.

After lyophilization the dried sponges may be packed together with desiccants in water vapor impermeable pouches and may be further gamma-sterilized, e.g. with 25kGray.

Example 2: Collagen Sponges Treated with EtOH-Solution of Two Reactive PEGs

COH102 and COH206 are dissolved in completely dried EtOH. PEG-concentrations (COH102 and COH206 1:1) of 10 mg/cm$^3$, 35 mg/cm$^3$, 70 mg/cm$^3$ and 100 mg/cm$^3$ are prepared and the solutions are filled into 9×7 cm PET-trays. Commercial available bovine collagen sponges (Matristypt®), 9×7 cm, with the same volume as the previously filled PEG-solution are placed on the top of the solutions. After absorption of the PEG-solution the collagen materials are dried in a vacuum chamber.

Dried sponges may be packed together with desiccants in water vapor impermeable pouches and may be gamma-sterilized, e.g. with 25kGray.

Example 3: Preparation of Collagen-/Reactive PEG Constructs 22 ml of aqueous, acidic solutions (pH 3.0, HCl) containing various concentrations (2.15 mg/cm$^3$, 4.3 mg/cm$^3$ and 7.2 mg/cm$^3$ of bovine corium collagen and PEG (COH102 and COH206 1:1)-concentrations of 7.2 mg/cm$^3$, 14.3 mg/cm$^3$, 28.6 mg/cm$^3$ and 57.3 mg/cm$^3$ are prepared, filled into PET-trays and lyophilized.

The dried sponges may be packed together with desiccants in water vapor impermeable pouches and may be gamma-sterilized, e.g. with 25kGray.

Example 4: Preparation of Two Layer Collagen-/Reactive PEG Constructs 11 ml and 22 ml of acidic collagen-/PEG-solutions (pH 3.0, HCl) as described in example 3 are filled into PET-trays and immediately frozen at −20° C. On the top of the ice phase 11 ml or 22 ml of a 1% bovine corium collagen solution, pH 3.0 (HCl) are applied and the constructs obtained are freeze-dried.

The dried sponges may be packed together with desiccants in water vapor impermeable pouches and may be gamma-sterilized, e.g. with 25kGray.

Example 5: Homogeneous Coating of Collagen Sponges with Reactive PEGs

A 1:1 powder mixture of COH102 and COH206 is homogeneously distributed onto one surface of a commercially available collagen sponge or on a sponge prepared after one of the methods as described in example 1, 2, 3 and 4. PEG-amounts of 2 mg/cm$^2$, 7 mg/cm$^2$, 10 mg/cm$^2$, 14 mg/cm$^2$ and 20 mg/cm$^2$ are used for the coating. The PEG-powder mixture is fixed on the surface of the sponge, e.g. by melting, such as by placing the sponges with the PEG-powder mixture into a preheated oven at 60 to 65° C. for 4 minutes.

The dried sponges may be packed together with desiccants in water vapor impermeable pouches and may be gamma-sterilized, e.g. with 25kGray.

Example 6: Discontinuous Coating of Collagen Sponges with Reactive PEGs

Pads are prepared as described in example 5 with the exception that before coating a grid is placed onto the surface of the collagen sponge, so that the surface of the pad is partially shielded and partially not covered by the PEG powder. Grid matrices with a mesh size of 5 mm and 10 mm are used and removed after powder distribution. Fixation of the powder, packaging and sterilization are those as described in example 5.

These prototypes allow a better penetration of the blood into the collagen pad, where coagulation occurs due to the procoagulant activity of collagen. The reactive PEGs assure the adhesion of the pad to the wound surface.

Example 7: Preparation of Constructs of Collagen with Cross-Linked PEG a) Onto a bovine collagen sponge the reactive PEGs COH102 and COH206 (1:1) are sprayed with a commercial available spray applicator composed of a double syringe and a gas driven spray head (Duplospray, Baxter). One syringe contains COH102 and COH206 at pH 3.0 and the second syringe buffer, pH 9.4. The polymerization of the two PEG-components occurs on the surface of collagen immediately after deposition. The sponge may be dried in a vacuum chamber.

b) A collagen sponge is treated with an acidic PEG-solution as described in example 1. In order to start the cross-linking between the two PEG-components and the collagen matrix, the wet sponge is treated with a basic buffer system and may be lyophilized afterwards.

Example 8: Continuous Coating of a Chitosan-/Gelatin Sponge with Reactive PEG's

A 1:1 powder mixture of COH102 and COH206 is homogeneously distributed onto one surface of a commercially available chitosan-/gelatin (Chitoskin®, Beese Medical) sponge. A PEG-amount of 14 mg/cm$^2$ is used for the coating. The PEG-powder mixture is fixed on the surface of the sponge, e.g. by melting, such as by placing the sponges with the PEG-powder mixture into a preheated oven at 60 to 65° C. for 4 minutes.

The dried sponges may be packed together with desiccants in water vapor impermeable pouches and may be gamma-sterilized, e.g. with 25kGray.

Example 9: Coating of an Oxidized Cellulose Fabric with Reactive PEG's

A 1:1 powder mixture of COH102 and COH206 is homogeneously distributed onto one surface of a commercially available oxidized cellulose fabric (Traumstem®, Bioster). A PEG-amount of 14 mg/cm$^2$ is used for the coating. The PEG-powder mixture is fixed on the surface of the sponge, e.g. by melting, such as by placing the sponges with the PEG-powder mixture into a preheated oven at 60 to 65° C. for 4 minutes.

The dried sponges may be packed together with desiccants in water vapor impermeable pouches and may be gamma-sterilized, e.g. with 25kGray.

Example 10: Preclinical Applications

Figure 2:
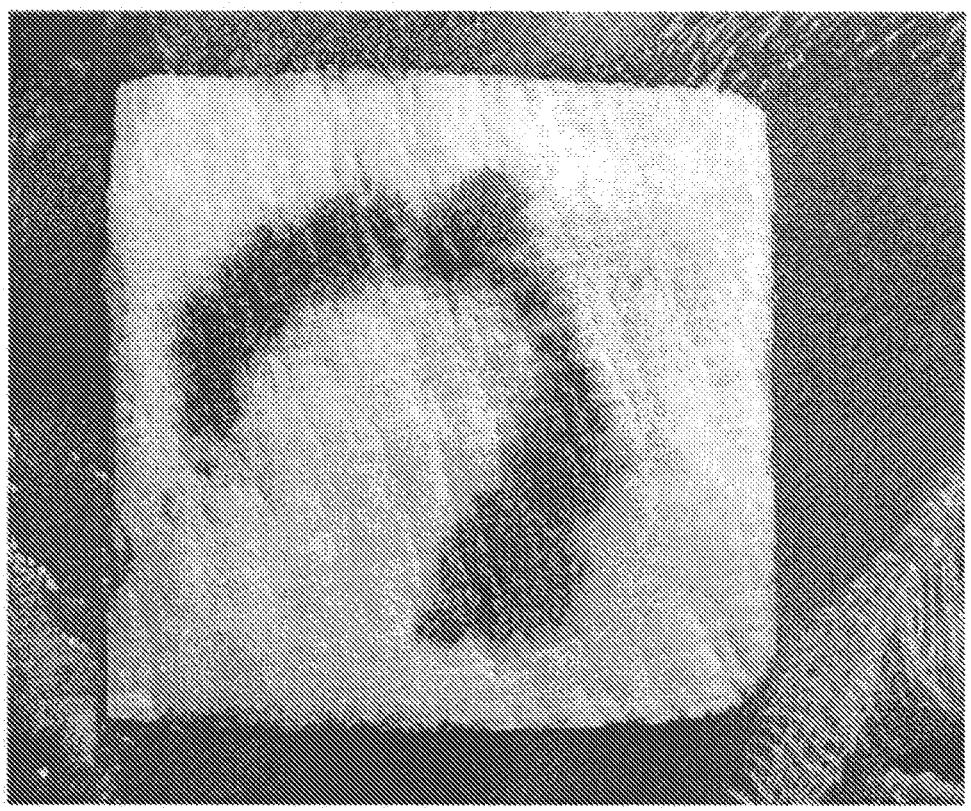
Figure 3:
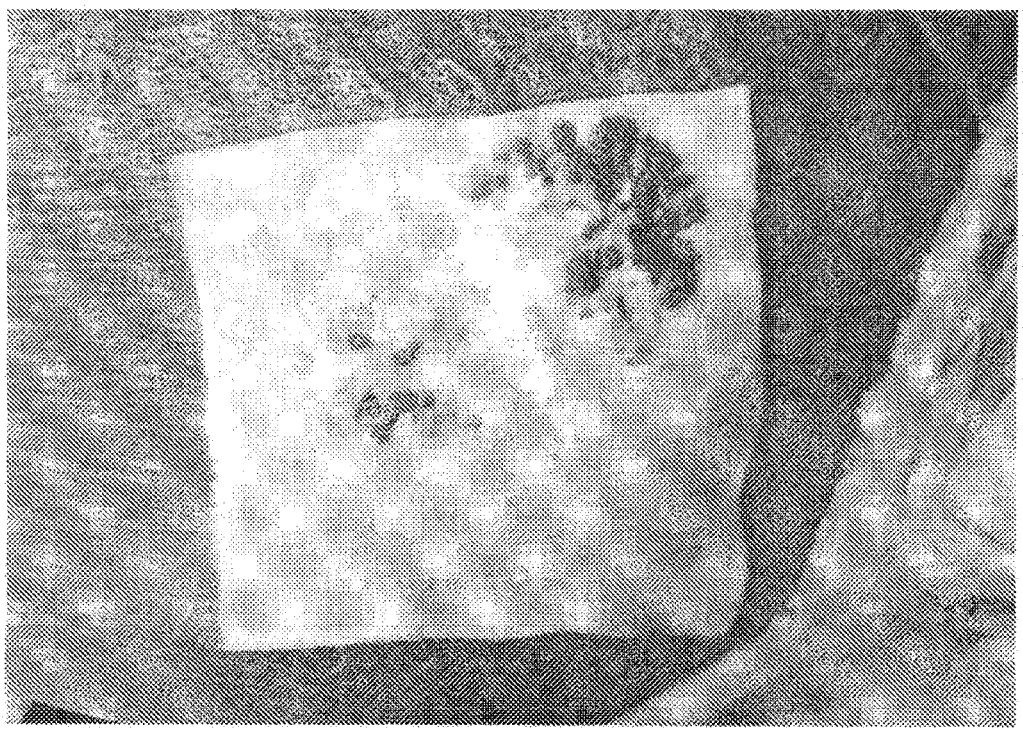
Figure 4:

A sponge as prepared according to the examples is tested in heparinized pigs (1.5-fold ACT) in a liver abrasion model. With a rotating grinding machine a circular bleeding wound with a diameter of 1.8 em is created on the surface of a liver lobe. A 3×3 em sponge is applied and moderately pressed against the wound for 2 minutes with a piece of gauze soaked with saline buffer. After removal of the gauze a good hemostatic performance is achieved as shown in FIGS. 1 to 4.

What is claimed is:

1. A hemostatic porous sponge comprising a matrix of oxidized cellulose and a bioadhesive material stably associated with at least one surface of said porous sponge, wherein said bioadhesive material is free of gelatin, said bioadhesive material is present in a range of 5 to 50 mg/cm$^2$ of the oxidized cellulose, and said bioadhesive material is present in a grid pattern on the porous sponge.

2. The sponge according to claim 1, wherein the bioadhesive material is selected from the group consisting of polyethylene glycol, derivatives of polyethylene glycol, and combinations thereof.

3. The sponge according to claim 1, wherein the bioadhesive material is reactive polyethylene glycol.

4. The sponge according to claim 1, wherein the bioadhesive material comprises multiple reactive polyethylene glycols.

5. The sponge according to claim 1, wherein the grid pattern forms a continuous layer on the surface of the sponge.

6. The sponge according to claim 1, wherein the bioadhesive material comprises a mixture of two pre-polymers comprising a first cross-linkable component and a second cross-linkable component that cross-links with the first cross-linkable component under reaction enabling conditions, and the second cross-linkable component comprises a polyethylene glycol (PEG) having two or more succinimidyl groups.

7. A hemostatic porous sponge comprising a matrix of oxidized cellulose and a material enhancing the adherence of said sponge to an applied tissue stably associated with at least one surface of said porous sponge, wherein said adherence-enhancing material is essentially free of gelatin, said adherence-enhancing material is present in a range of 5 to 50 mg/cm$^2$ of the oxidized cellulose, and the adherence-enhancing material is present in a grid pattern on the porous sponge.

8. The sponge according to claim 7, wherein the adherence-enhancing material is selected from the group consisting of polyethylene glycol, derivatives of polyethylene glycol, and combinations thereof.

9. The sponge according to claim 7, wherein the adherence-enhancing material is reactive polyethylene glycol.

10. The sponge according to claim 7, wherein the adherence-enhancing material comprises multiple reactive polyethylene glycols.

11. The sponge according to claim 7, wherein the grid pattern forms a continuous layer on the surface of the sponge.

12. The sponge according to claim 7, wherein the sponge comprises multiple polymers.

13. The sponge according to claim 7, wherein the adherence-enhancing material comprises a mixture of two pre-polymers comprising a first cross-linkable component and a second cross-linkable component that cross-links with the first cross-linkable component under reaction enabling conditions, and the second cross-linkable component comprises a polyethylene glycol (PEG) having two or more succinimidyl groups.

14. A hemostatic porous sponge comprising a matrix of oxidized cellulose and a gelatin-free material enhancing the adherence of said sponge to an applied tissue stably associated with at least one surface of said porous sponge, wherein said gelatin-free material is present in a range of 5 to 50 mg/cm$^2$ of the oxidized cellulose, wherein the gelatin-free material is present in an organized pattern on the porous sponge.

15. The sponge according to claim 14, wherein the gelatin-free material is selected from the group consisting of polyethylene glycol, derivatives of polyethylene glycol, and combinations thereof.

16. The sponge according to claim 14, wherein the gelatin-free material is reactive polyethylene glycol.

17. The sponge according to claim 14, wherein the gelatin-free material comprises multiple reactive polyethylene glycols.

18. The sponge according to claim 14, wherein the organized pattern forms a continuous layer on the surface of the sponge.

19. The sponge according to claim 14, wherein the sponge comprises multiple polymers.

20. The sponge according to claim 14, wherein the gelatin-free material comprises a mixture of two pre-polymers comprising a first cross-linkable component and a second cross-linkable component that cross-links with the first cross-linkable component under reaction enabling conditions, and the second cross-linkable component comprises a polyethylene glycol (PEG) having two or more succinimidyl groups.

\* \* \* \* \*